(12) United States Patent
Komatsu et al.

(10) Patent No.: US 10,350,097 B2
(45) Date of Patent: Jul. 16, 2019

(54) STENT DELIVERY SYSTEM

(71) Applicant: TERUMO KABUSHIKI KAISHA, Shibuya-ku, Tokyo (JP)

(72) Inventors: Tomoya Komatsu, Hadano (JP); Takashi Kumazawa, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 37 days.

(21) Appl. No.: 15/696,471

(22) Filed: Sep. 6, 2017

(65) Prior Publication Data
US 2018/0064567 A1 Mar. 8, 2018

(30) Foreign Application Priority Data
Sep. 8, 2016 (JP) .................. 2016-175965

(51) Int. Cl.
*A61F 2/958* (2013.01)
*A61F 2/88* (2006.01)
*A61F 2/915* (2013.01)
*A61M 25/10* (2013.01)

(52) U.S. Cl.
CPC .............. *A61F 2/958* (2013.01); *A61F 2/88* (2013.01); *A61F 2/915* (2013.01); *A61F 2002/91508* (2013.01); *A61F 2002/91516* (2013.01); *A61F 2002/91525* (2013.01); *A61F 2002/91575* (2013.01); *A61F 2002/91583* (2013.01); *A61F 2002/91591* (2013.01); *A61F 2210/0004* (2013.01); *A61F 2210/0076* (2013.01); *A61F 2230/0091* (2013.01); *A61F 2250/0067* (2013.01); *A61F 2250/0071* (2013.01); *A61M 25/1006* (2013.01); *A61M 2025/1086* (2013.01)

(58) Field of Classification Search
CPC .... A61F 2/958; A61F 2/88; A61F 2/82; A61F 2/915
See application file for complete search history.

(56) References Cited

U.S. PATENT DOCUMENTS

| 8,333,799 | B2 | 12/2012 | Bales, Jr. et al. | |
| 2007/0208406 | A1* | 9/2007 | Alkhatib | A61F 2/954 623/1.11 |
| 2008/0243221 | A1* | 10/2008 | Arcand | A61F 2/958 623/1.11 |

* cited by examiner

*Primary Examiner* — Jason-Dennis N Stewart
(74) *Attorney, Agent, or Firm* — Buchanan Ingersoll & Rooney PC (57) ABSTRACT

To provide a stent delivery system configured to prevent twisting of a strut during expansion of a stent. A balloon has a plurality of limb portions folded at a plurality of folding pleats in a deflated state. The limb portions are folded in a first circumferential direction to surround the shaft as seen from a proximal end side of an axial direction of the shaft. The strut of the stent has helical portions formed in a helical shape extending along a second circumferential direction opposite to the first circumferential direction as seen from the proximal end side of the axial direction with being centered on an axis extending along the axial direction of the shaft.

20 Claims, 6 Drawing Sheets

STENT DELIVERY SYSTEM

CROSS-REFERENCES TO RELATED APPLICATIONS

This application claims priority to Japanese application number No. 2016-175965 filed on Sep. 8, 2016, the entire content of which is incorporated herein by reference.

TECHNICAL FIELD

The present invention generally relates to a stent delivery system.

BACKGROUND DISCUSSION

A stent is indwelled in a stenosed or stricture site in a lumen of a living body such as a blood vessel in an expanded state to maintain an open state of the lumen of the living body. Therefore, the stent is required to have strength for holding the expanded state. The stent is also required to have flexibility to follow a shape of the lumen of the living body, and various studies have been made for improving flexibility.

For example, U.S. Pat. No. 8,333,799 discusses a stent provided with a strut formed in a helical shape. The strut formed in a helical shape has higher flexibility compared to a strut formed in an annular shape. Therefore, the stent can appropriately follow the shape of the lumen of the living body.

SUMMARY

However, in order to indwell stent in a lesion area, a balloon catheter is typically employed as a delivery device. The stent is arranged on an outer surface of a balloon folded to surround a shaft in a deflated state, so that the stent is expanded as the balloon is inflated.

However, the strut formed in a helical shape is easily twisted, compared to the strut formed in an annular shape. Therefore, in some cases, the strut may be twisted when the stent is expanded by inflating the balloon. If the strut is indwelled in a lumen of a living body in the twisted state, the stent may be re-coiled.

The inventors made diligent studies to address the aforementioned problems. As a result, the inventors discovered that the twist of the strut can be inhibited or prevented if a balloon folding direction is opposite to a helical extending direction of the strut of the stent as seen from a proximal end side of a delivery device in an axial direction thereof.

The stent delivery system disclosed here is configured to inhibit or prevent twisting of the strut when the stent is expanded.

According to one disclosed aspect, there is provided a stent delivery system including: a balloon catheter comprised of an elongated shaft and an inflatable/deflatable balloon provided at a distal end side of the shaft; and a stent provided on an outer surface of the balloon while the balloon is deflated. The deflated balloon comprises a plurality of limb portions folded at a plurality of folding pleats that extend along an axial direction of the shaft, with the plurality of limb portions being folded in a first circumferential direction to surround the shaft as seen from a proximal end side of the shaft in the axial direction. The stent is comprised of a strut that includes a helical portion formed in a helical shape and helically extending along a second circumferential direction opposite to the first circumferential direction as seen from the proximal end side of the shaft in the axial direction centered on an axis extending along the axial direction of the shaft.

Using the stent delivery system disclosed here, a movement direction of the limb portion caused by inflation of the balloon is in the same direction as a helical extending direction of the stent as seen from the proximal end side of the axial direction of the shaft. Since the helical portion receives a force in the helical extending direction as the limb portion moves, the helix evenly expands, so that it is possible to prevent a twist of the stent. As a result, it is possible to prevent re-coiling of the indwelled stent.

In accordance with another aspect of the disclosure here, a stent delivery system comprises: an inner tube positioned inside an outer tube, with a lumen between the inner tube and the outer tube, the outer tube possessing a distal end portion, and the inner tube possessing a distal end portion; a balloon possessing an outer surface, an interior, a proximal end portion fixed to the distal end portion of the outer tube, and a distal end portion fixed to the distal end portion of the inner tube, the lumen between the inner and outer tubes communicating with the interior of the balloon to introduce fluid into the balloon to outwardly expand the balloon from a deflated state to an inflated state; the balloon in the deflated state comprising a plurality of circumferentially spaced apart limb portions each folded at a respective folding pleat in a first circumferential direction as viewed from the proximal end portion of the balloon along an axial direction of the balloon so that the limb portions are in an overlying position in which the limb portions are in overlying relation to an underling portion of the balloon, the limb portions moving in a second circumferential direction opposite the first circumferential direction and away from the overlying position when the fluid is introduced into the balloon and the balloon outwardly expands from the deflated state toward the inflated state; a stent encircling the outer surface of the balloon in the deflated state, the stent possessing a proximal end portion and a distal end portion; and the stent being comprised of a strut that includes a helical portion, the helical portion extending helically in the second circumferential direction from a position adjacent the proximal end portion of the stent toward the distal end portion of the stent as viewed from the proximal end portion of the balloon along an axial direction of the balloon.

According to another aspect, a method comprises: delivering a stent to a lesion area in a lumen of a living body, wherein the stent encircles an outer surface of a balloon while the balloon is in a deflated state, and the balloon possesses a proximal end portion. The balloon in the deflated state comprises a plurality of circumferentially spaced apart limb portions each folded at a respective folding pleat in a first circumferential direction as viewed from the proximal end portion of the balloon along an axial direction of the balloon so that the limb portions are in an overlying position in which the limb portions are in overlying relation to an underling portion of the balloon. The stent possesses a proximal end portion and a distal end portion, and the stent comprises a strut that includes a helical portion extending helically toward the distal end portion of the stent as viewed from the proximal end portion of the balloon along the axial direction of the balloon, with the second circumferential direction being opposite the first circumferential direction. The method further comprises outwardly expanding the balloon that is in the deflated state so that the balloon undergoes outward expansion in which the balloon outwardly expands toward an expanded state. The outward expansion of the balloon applies an outwardly directed force to the stent causing the limb portions of the stent to move in the second circumferential direction away from the overlying position as the stent expands outwardly.

DETAILED DESCRIPTION

Set forth below with reference to the accompanying drawings is a detailed description of embodiments of a stent delivery system representing examples of the inventive stent delivery system disclosed here. The dimensions or scales on the drawings may be exaggerated or different from actuality/reality for convenience of description and illustration.

DETAILED DESCRIPTION

The following description is not intended to limit the technical scope or meanings of terminologies described in the claims. Furthermore, dimensions or scales on the drawings are exaggerated for purposes of better understanding and may be different from those of the reality.

A stent delivery system 10 is used to deliver a stent 200 to a lesion area such as a stenosed site in a lumen of a living body such as a blood vessel, a bile duct, an esophagus, a trachea, and a urethra using a balloon catheter 100.

Figure 1:
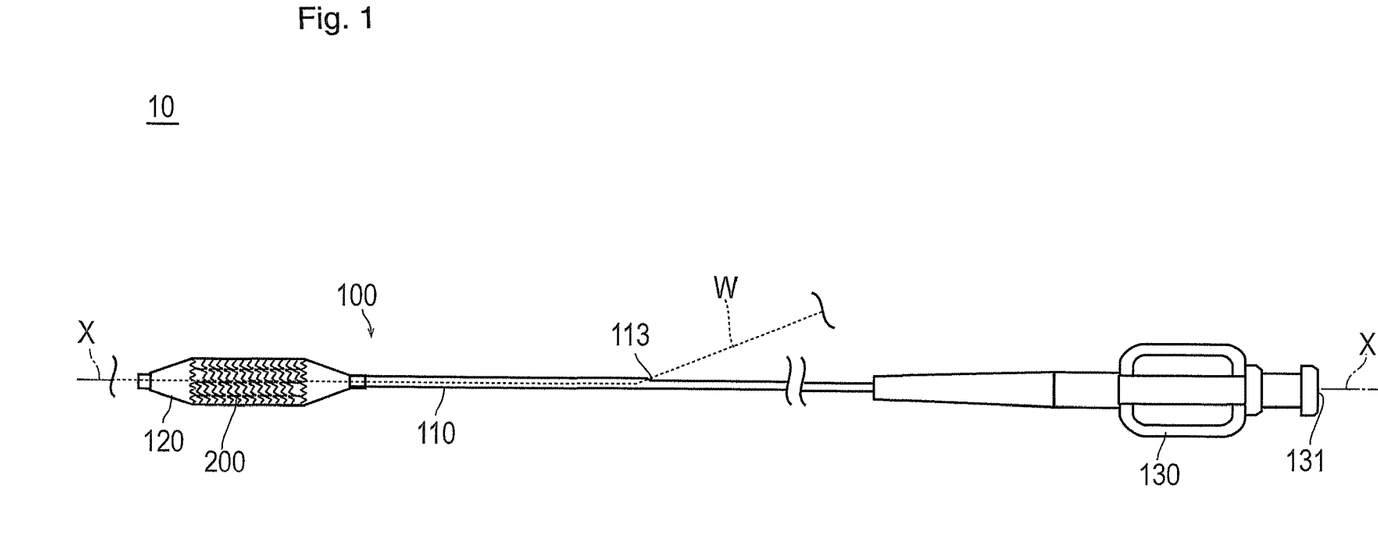
FIG. 1 is a simplified diagram illustrating a whole configuration of a stent delivery system according to an embodiment.

As illustrated in FIG. 1, the stent delivery system 10 has the balloon catheter 100 and the stent 200. In the description below, the side inserted into a living body is referred to as a "distal end" or "distal end side," and a near side is referred to as a "proximal end" or "proximal end side."

Configurations of each part of the stent delivery system 10 will now be described.

The balloon catheter 100 includes a long (elongated) shaft 110, an inflatable/deflatable balloon 120 provided at a distal end side of the shaft 110, and a hub 130 fixed to a proximal end of the shaft 110. The stent 200 is mounted and encircles on an outer circumferential surface of the balloon 120.

Figure 2A:
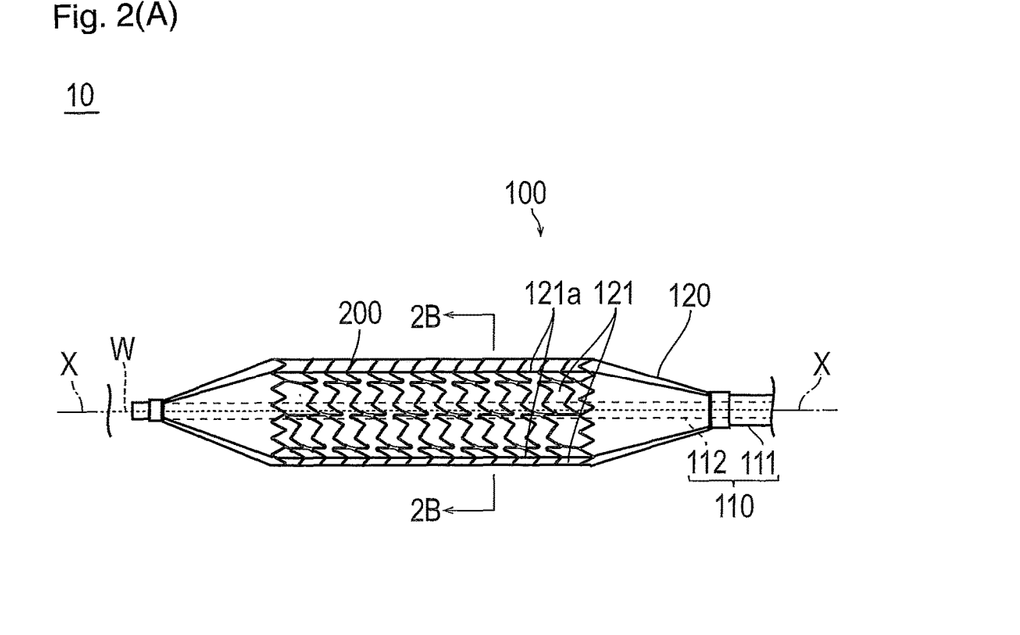
FIG. 2(A) is an enlarged view illustrating a balloon and a stent in a deflated state.

As illustrated in FIG. 2(A), the shaft 110 extends along an axial direction and includes an outer tube 111 which is a tubular body open at both the distal and proximal ends, and an inner tube 112 arranged in a cavity or lumen of the outer tube 111.

A dilation lumen where a dilation fluid for inflating the balloon 120 flows is provided between the outer tube 111 and the inner tube 112. A guide wire lumen where a guide wire W for guiding the balloon 120 to a lesion area is inserted is provided inside the inner tube 112. The dilation fluid may be a gas or a liquid. For example, the dilation fluid may include a gas such as a helium gas, a $CO_2$ gas, and an $O_2$ gas, or a liquid such as saline or a contrast agent.

The balloon catheter 100 according to this embodiment is a so-called rapid exchange type catheter in which the guide wire W is introduced into the inner tube 112 through a guide wire opening 113 formed between the distal end side and the proximal end side of the shaft 110 as illustrated in FIG. 1. Alternatively, the balloon catheter 100 may be a so-called over-the-wire catheter.

Figure 3:
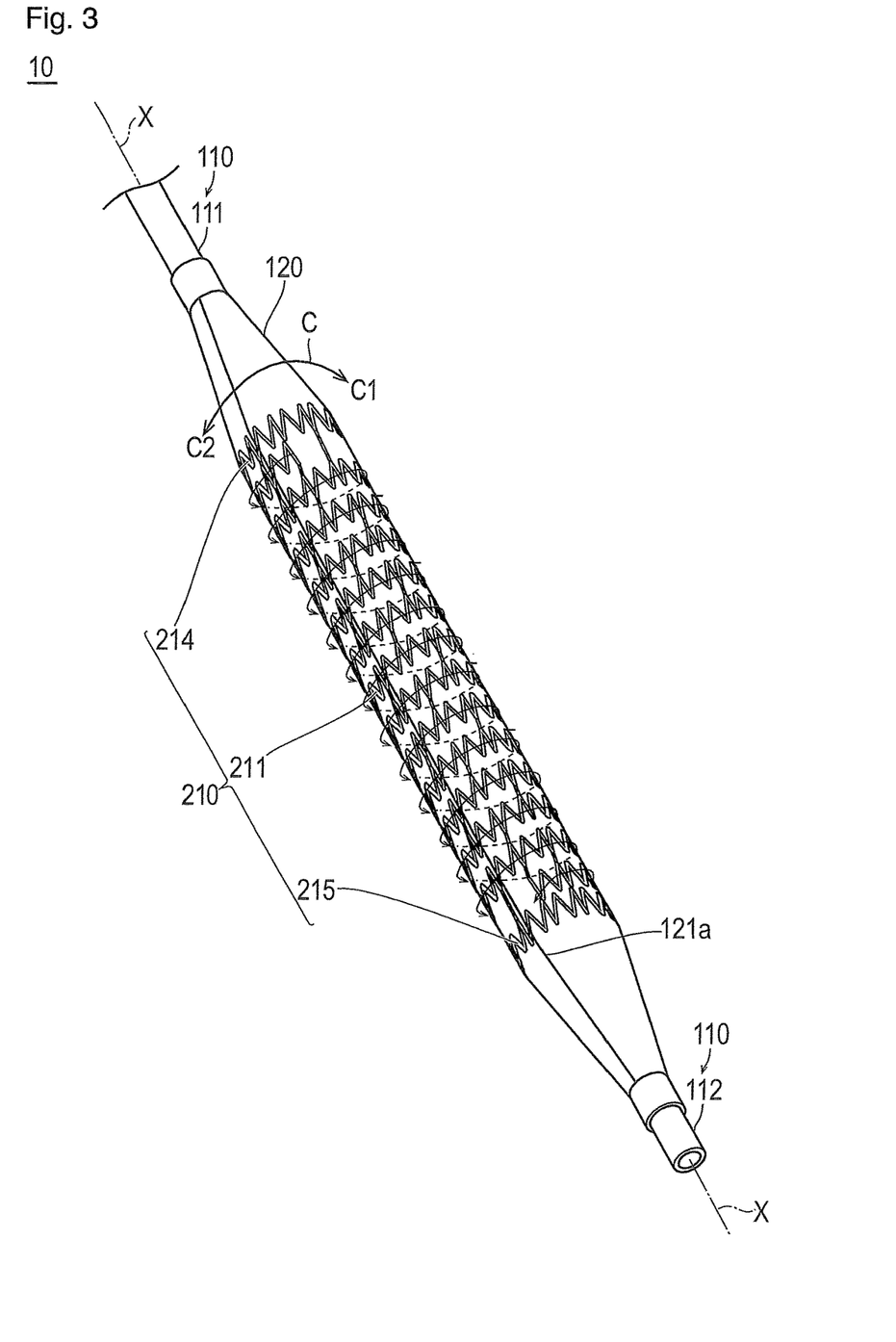
FIG. 3 is an enlarged perspective view illustrating a distal end portion of the stent delivery system according to an embodiment.

As illustrated in FIGS. 2(A) and 3, a distal end portion of the inner tube 112 penetrates through the balloon 120 and is opened on the distal end side relative to the balloon 120.

The outer tube 111 and the inner tube 112 are preferably formed of a material having a certain degree of flexibility. Such a material may include, for example, polyolefins such as polyethylene, polypropylene, polybutene, ethylene-propylene copolymer, ethylene-vinyl acetate copolymer, ionomer, and a mixture of two or more of them, thermoplastic resin such as polyvinyl chloride resin, polyamide, a polyamide elastomer, polyester, a polyester elastomer, polyurethane, and fluororesin, silicon rubber, latex rubber, or the like.

The balloon 120 is inflated to expand the stent 200. A proximal end portion of the balloon 120 is fixed to a distal end portion of the outer tube 111, and a distal end portion of the balloon 120 is fixed to a distal end portion of the inner tube 112.

Figure 2B:
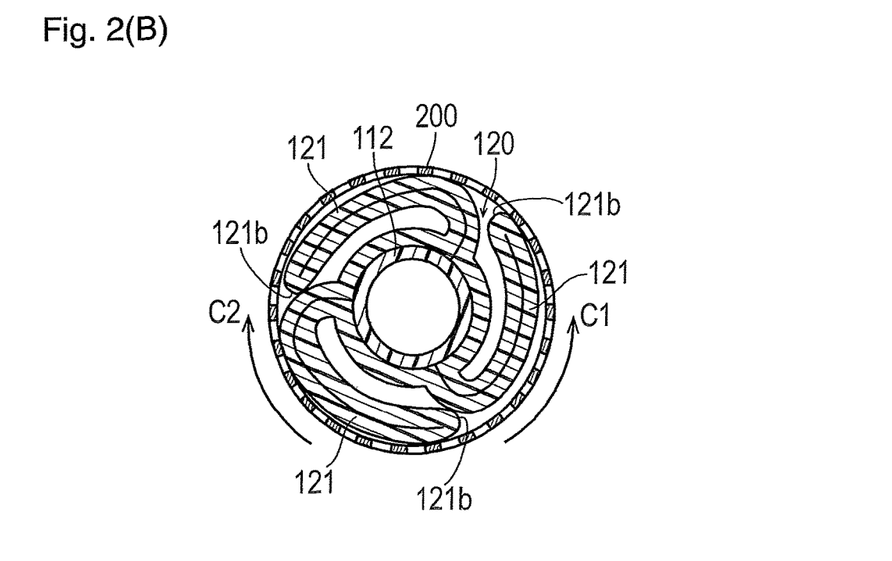
FIG. 2(B) is an enlarged cross-sectional view taken along the line 2B-2B of FIG. 2(A).

In a deflated state, the balloon 120 has a plurality of limb portions or wing-like (wing-shaped) portions 121 folded at a plurality of folding pleats or folding lines 121a as illustrated in FIG. 2(A) so that the limb portions 121 overlie underlying portions of the balloon as shown in FIG. 2(B). The limb portions 121 are somewhat wing-like portions or wing-shaped portions. As illustrated in FIG. 2(B), the limb portions 121 are folded in a first circumferential direction C1 (counterclockwise) to surround the inner tube 112 as seen from the proximal end side along the axial direction X. Each limb portion 121 has a peak portion 121b (end portion) formed by folding the balloon 120 in a mountain shape outward in a radial direction of the balloon 120. The folding pleat 121a is formed by a ridge extending in the axial direction X from the peak portion 121b. Here, the first circumferential direction C1 and a second circumferential direction C2 described below will be collectively referred to as a "circumferential direction C."

The limb portion 121 is preferably formed nearly in the same direction as the circumferential direction C of the balloon 120. According to this embodiment, as illustrated in FIG. 2(B), the balloon 120 is provided with three limb portions 121 arranged or circumferentially spaced at an angle of about 120° along the circumferential direction C of the balloon 120. The number of limb portions 121 is not particularly limited as long as it is three or larger, and may be four or larger.

The balloon 120 is preferably formed of a material having a certain degree of flexibility. For example, the balloon 120 may be formed of polyolefins such as polyethylene, polypropylene, polybutene, ethylene-propylene copolymer, ethylene-vinylacetate copolymer, ionomer, or a mixture of two or more of them, thermoplastic resin such as soft polyvinyl chloride resin, polyamide, polyamide elastomer, polyester, polyester elastomer, polyurethane, or fluororesin, silicone rubber, latex rubber, and the like.

As illustrated in FIG. 1, the hub 130 has a proximal end opening 131 serving as a port for introducing the dilation fluid. This proximal end opening 131 communicates with a dilation lumen formed in the outer tube 111.

The hub 130 may be formed of, for example, thermoplastic resin such as polycarbonate, polyamide, polysulfone, polyarylate, and methacrylate-butylene-styrene copolymer.

Figure 4:
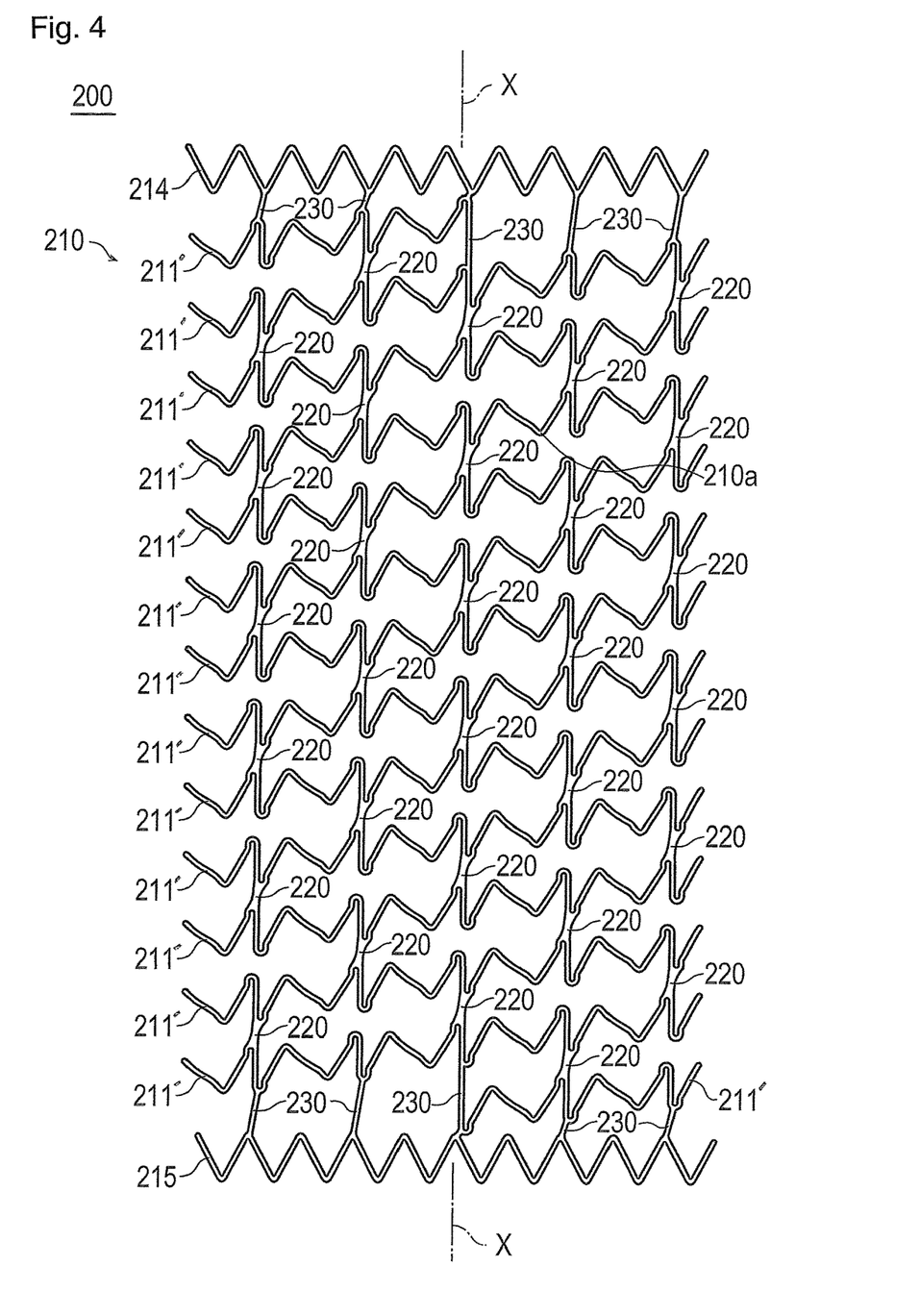
FIG. 4 is an exploded view illustrating a part of an outer circumference of the stent according to the embodiment by cutting away straightly along an axial direction.

The stent 200 is a so-called balloon inflation type stent which is expanded (plastically deformed) by an inflation force of the balloon 120. As illustrated in FIG. 4, the stent 200 has a strut 210 as a linear element and a plurality of link portions 220 and 230. The strut 210 forms a tubular outer periphery provided with openings as illustrated in FIG. 3. The strut 210 is provided with a plurality of meandering folded portions 210a folded in a wave shape (refer to FIG. 4) so that the meandering portions 210a are wavy-shaped.

The axial direction and the circumferential direction of the cylindrical shape of the stent 200 are in the same direction as the axial direction X and the circumferential direction C of the shaft 110 while the stent 200 is mounted on the balloon 120 as illustrated in FIG. 1, and so the axial direction of the cylindrical shape will be referred to as the "axial direction X," and the circumferential direction of the cylindrical shape will be referred to as the "circumferential direction C" using the same reference signs.

The strut 210 has annular portions 214 and 215 that are respectively positioned at opposite ends of the stent in the axial direction X and that extend in the circumferential direction C so that each annular portion 214, 215 forms an endless annular shape. The strut 210 also includes a plurality of helical segments or parts 211' each extending in a helical manner and located between the annular portion 214 and the annular portion 215. As illustrated, the helical segments or parts 211' may be integrated with each other so that the helical segments or parts 211' collectively form a helical portion 211 (single helical portion) that extends continuously in a helical manner from the annular portion 214 at one axial end of the stent to the annular portion 215 at the opposite axial end of the stent as shown in FIG. 3.

As illustrated in FIG. 3, the helical portion 211 has a helical shape extending toward the distal end direction along the second circumferential direction C2 (clockwise) opposite to the first circumferential direction C1 as seen from the proximal end side of the axial direction X while being centered on an axis extending in the axial direction X of the shaft 110. That is, the helical portion 211 has a helix formed by rotatingly advancing a right-handed screw (right-handed helix). Thus, as viewed along the axial direction from the proximal end of the stent, the helical portion 211 extends helically in the second circumferential direction C2 from the annular portion 214 at the proximal end of the stent to the annular portion 215 at the distal end of the stent. The proximal end or proximal end side is the left or upper end in FIG. 3, and is the right end in FIG. 2(B).

The helical portion 211 is crimped or in a contracted state while it is arranged to cover the balloon 120 folded to surround the outer circumference of the inner tube 112 in a deflated state, so that it is held in place and covers the outer circumference of the balloon 120 as illustrated in FIGS. 2(A), 2(B), and 3.

A material of the strut 210 is, for example, a non-biodegradable material that is not degraded in a living body. Such a material includes, for example, stainless steel, cobalt-based alloy such as cobalt-chromium alloy (for example, CoCrWNi alloy), elastic metal such as platinum-chromium alloy (for example, PtFeCrNi alloy), super-plastic alloy such as nickel-titanium alloy, or the like.

As illustrated in FIG. 4, each of the link portions 220 connects neighboring or axially adjacent helical segments 211' of the helical portion 211 and spans the gap between the axially adjacent helical segments 211'. The link portions 220 are arranged to cross a separation direction of the neighboring helical segments 211 with a gap at a predetermined interval. The link portions 220 may thus spaced apart at regular intervals in the circumferential and helical direction as illustrated by way of example in FIG. 4.

Figure 5A:
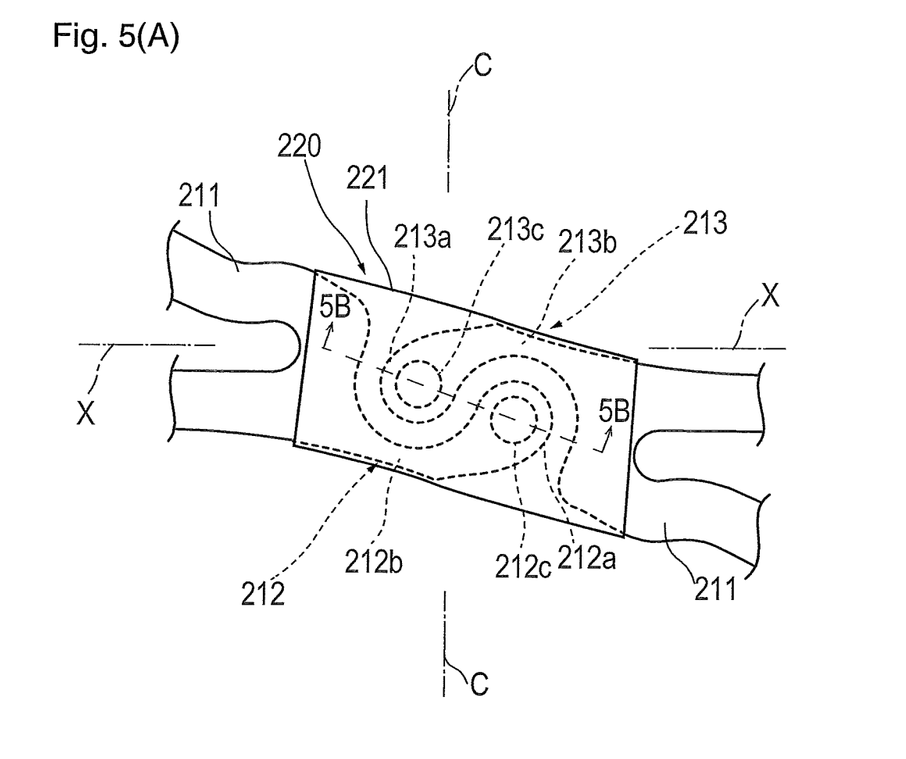
FIG. 5(A) is an enlarged view illustrating a link portion of the stent according to the embodiment.

As illustrated in FIG. 5(A), the link portions 220 each include a first connecting portion 212, a second connecting portion 213, and a biodegradable polymer 221. In the description herein, the first and second connecting portions 212 and 213 are collectively referred to as "connecting portions 212 and 213."

Figure 5B:
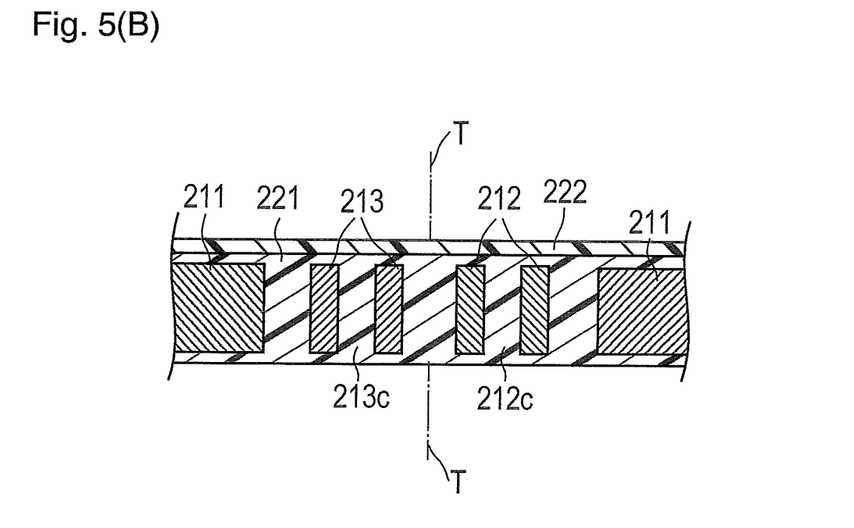
FIG. 5(B) is an enlarged cross-sectional view taken along the line 5B-5B of FIG. 5(A).

Each of the connecting portions 212 and 213 is provided integrally with a respective one of the neighboring helical parts 211 (e.g., the connecting portions are integral extensions of the neighboring helical parts), and the connecting portions 212 and 213 may be connected by the biodegradable polymer 221 while so that the connecting portions 212 and 213 face each other such as shown in FIG. 5(B).

Each of the first connecting portions 212 may be formed such that one of the two neighboring helical parts 211' partially protrudes towards the neighboring or adjacent helical part 211'. Each of the second connecting portions 213 may be formed such that the other helical part 211' partially protrudes towards the neighboring or adjacent helical part.

As illustrated in FIGS. 5(A) and 5(B), each first connecting portion 212 includes a protruding portion 212a protruding toward the second connecting portion 213 side and having a rounded curved shape, a receiving portion 212b that continues from the protruding portion 212a and has a concave shape matching an exterior shape of the protruding portion 213a of the second connecting portion 213, and a holding portion 212c that penetrates in the thickness direction T of the stent 200 (hereinafter, simply referred to as a "thickness direction T") from the surface of the helical portion 211 to hold the biodegradable polymer 221. Each second connecting portion 213 includes a protruding portion 213a protruding toward the first connecting portion 212 side and having a rounded curved shape, a receiving portion 213b that continues from the protruding portion 213a and has a concave shape matching an exterior shape of the protruding portion 212a of the first connecting portion 212, and a holding portion 213c that penetrates in the thickness direction T from the surface of the helical portion 211 to hold the biodegradable polymer 221.

The concave shape of the receiving portion 212b is larger than the exterior shape of the protruding portion 213a. In addition, the concave shape of the receiving portion 213b is larger than the exterior shape of the protruding portion 212a.

As illustrated in FIG. 5(A), the protruding portion 212a is housed or positioned in the concave shape of the receiving portion 213b. The protruding portion 213a is formed to be housed or positioned in the concave shape of the receiving portion 212b.

The protruding portion 212a may partially contact the receiving portion 213b. In addition, the protruding portion 213a may partially contact the receiving portion 212b.

As illustrated in FIG. 5(B), according to this embodiment, each holding portion 212c and 213c has a penetrating hole that penetrates in the thickness direction T of the helical portion 211. Alternatively, each holding portion 212c and 213c may not have a penetrating hole as long as it can hold the biodegradable polymer 221, and may have a shape hollowed at least at a certain level in the thickness direction T of the helical portion 211 (e.g., a blind hole).

As illustrated in FIGS. 5(A) and 5(B), the biodegradable polymer 221 ties up or connects the first and second connecting portions 212 and 213 with each other until a predetermined time elapses, and the biodegradable polymer 221 is degraded after the stent 200 is indwelled in a lumen of a living body.

The biodegradable polymer 221 is provided so that the biodegradable polymer 221 integrally continues to the surfaces of the connecting portions 212 and 213 (the biodegradable polymer 221 covers the oppositely facing surfaces of the connecting portions 212 and 213), the gap between the first and second connecting portions 212 and 213, and the inside of each holding portion 212c and 213c. The biodegradable polymer 221 is provided to cover the surfaces of the connecting portions 212 and 213 and fill the gap between the first and second connecting portions 212 and 213, and the inside of each holding portion 212c and 213c, so that the connecting portions 212 and 213 are connected with each other more appropriately.

A material of the biodegradable polymer 221 is not particularly limited as long as it is polymer that is degraded in a living body. Such a material may include, for example, a biodegradable synthetic polymeric material such as polylactic acid, polyglycolic acid, lactic acid-glycolic acid copolymer, polycaprolactone, lactic acid-caprolactone copolymer, glycolic acid-caprolactone copolymer, polyglutamic acid, or a biodegradable natural polymer material such as collagen.

As illustrated in FIG. 5(B), the link portion 220 has a coating layer 222 containing a medicine on a surface of the biodegradable polymer 221. The coating layer 222 is formed on a surface of the biodegradable polymer 221, preferably, on an outer surface facing an inner circumferential surface of a lumen of a living body, but not limited thereto.

The coating layer 222 contains a medicine capable of preventing proliferation of a neointima and a medicine carrier for carrying the medicine. The coating layer 222 may contain only the medicine. The medicine contained in the coating layer 222 includes at least one selected from a group consisting of, for example, sirolimus, everolimus, zotarolimus, paclitaxel, and the like. A material of the medicine carrier preferably includes, but is not particularly limited to, a biodegradable material. The same material as that of the biodegradable polymer 221 may be applied.

The link portions 230 are formed integrally with the annular portions 214 and 215 and the adjacent or neighboring helical parts 211'.

Next, functional effects of the stent delivery system 10 according to this embodiment will be described.

Generally speaking, the stent delivery system 10 delivers the stent 200 to a stenosed site or a stricture site existing in a lumen of a living body such as a blood vessel, a bile duct, a trachea, an esophagus, or a urethra. The delivered stent 200 is then expanded and indwelled in a lesion area such as a stenosed site in a lumen of a living body.

Figure 6:
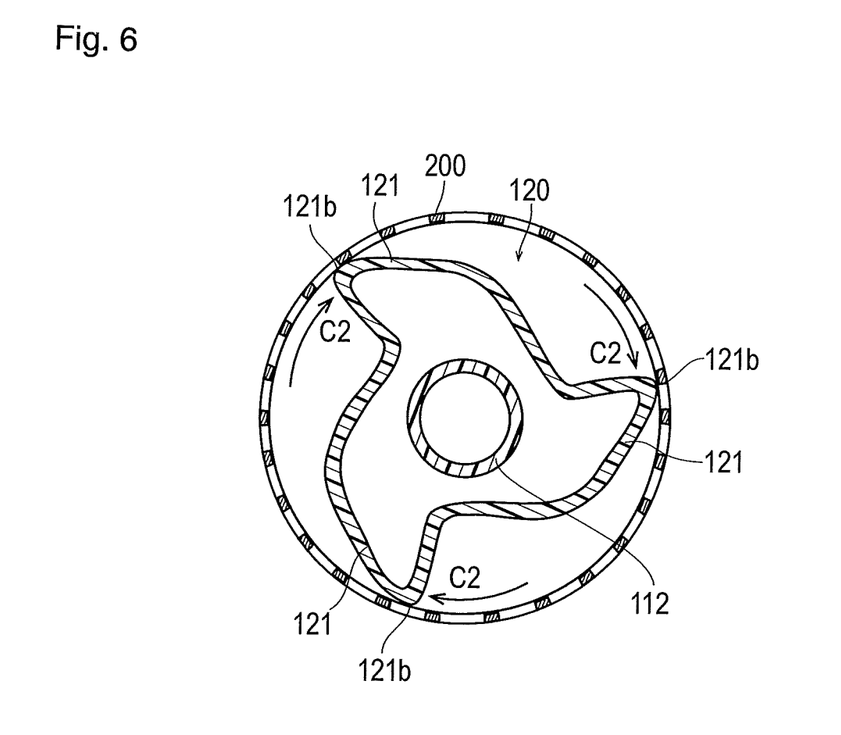
FIG. 6 is a cross-sectional view illustrating a situation in which the balloon is inflated, and the stent is expanded according to the embodiment.

More specifically, after the stent delivery system 10 is introduced into the living body and is operated to position the balloon 120 in a lesion area, the balloon 120 is inflated. As illustrated in FIG. 6, the balloon 120 is inflated such that the folded limb portions 121 are unfolded. The limb portions 121 make contact with the helical portion 211 and apply a force of expanding outward in a radial direction (outwardly expanding force). As the balloon 120 is inflated, the limb portion 121 is deformed and moves along the second circumferential direction C2. As the limb portion 121 moves, the helical portion 211 of the stent receives a force outward in a radial direction and in the second circumferential direction C2. In this manner, as the balloon 120 is inflated, the stent 200 receives a force in the second circumferential direction C2 which is in the same direction as the helical extending direction. Therefore, by evenly expanding a helix of the helical portion 211, it is possible to inhibit or prevent the stent 200 from being twisted.

If the helical portion 211 is formed in a helical shape that extends helically in the distal end direction along the first circumferential direction C1 as seen from the proximal end side of the axial direction X, the helical extending direction is opposite to the movement direction of the limb portion 121 caused by inflation of the balloon 120. As a result, outward expansion of the strut 210 having the helical portion 211 folded in a wave shape is delayed, so that the stent 200 has an uneven expansion state.

In the stent delivery system 10 according to this embodiment, the balloon 120 has a plurality of limb portions 121 folded at a plurality of folding pleats or folding lines 121a along the axial direction X of the shaft 110 in a deflated state. The limb portions 121 are folded in the first circumferential direction C1 to surround the shaft 110 as seen from the proximal end side of the axial direction X. The strut 210 of the stent 200 has the helical portion 211 formed or wound in a helical shape extending along the second circumferential direction C2 opposite to the first circumferential direction C1 as seen from the proximal end side of the axial direction X while being centered on an axis extending along the axial direction X.

In the aforementioned configuration, the movement direction of the limb portion 121 caused by inflation of the balloon 120 and the helical extending direction of the stent 200 are in the same direction (the second circumferential direction C2 as seen from the proximal end side of the axial direction X). Since the helical portion 211 receives a force in the helical extending direction as the limb portion 121 moves, the helix is relatively evenly expanded, so that it is possible to inhibit or prevent the stent 200 from being twisted. As a result, it is possible to inhibit or prevent the indwelled stent 200 from re-coiling and more effectively treat a lesion area.

A part of the stent 200 is formed by the biodegradable polymer 221. The part formed by the biodegradable polymer 221 has strength lower than that of a metal material and thus becomes a weak part. For this reason, a twist is rather easily generated in the stent 200 from this weak portion as a starting point. In this manner, even in the stent 200 that is easily twisted, the stent 200 has a configuration that is not easily twisted with respect to the balloon 120. Therefore, it is possible to prevent a twist that may be generated when the stent 200 is expanded and prevent re-coiling of the indwelled stent 200.

In addition, the stent 200 further has a link portion 220 that connects the neighboring helical portions 211 to each other, and at least one of the link portions 220 includes the biodegradable polymer 221. The helical portion 211 is formed of a metal material. For this reason, the link portion 220 becomes a relatively weak portion having strength lower than that of the helical portion 211, and the stent 200 is rather easily twisted from the link portion 220 as a starting point. In this manner, even in the stent 200 that is easily twisted, the stent 200 has a configuration that is not easily twisted with respect to the balloon 120. Therefore, it is possible to inhibit or prevent a twist that may be generated when the stent 200 is expanded and prevent re-coiling of the indwelled stent 200.

In addition, the link portions 220 are provided integrally with one of the neighboring helical parts 211' and the other helical part 211' and includes the first and second connecting portions 212 and 213 arranged to face each other and the biodegradable polymer 221 interposed between the first and second connecting portions 212 and 213 to connect the first and second connecting portions 212 and 213. The first connecting portion 212 has the protruding portion 212a that protrudes toward the second connecting portion 213 side and has a rounded curved shape and the receiving portion 212b that continues to the protruding portion 212a and has a concave shape matching the exterior shape of the protruding portion 213a. The second connecting portion 213 has the protruding portion 213a that protrudes toward the connecting portion 212 side and has a rounded curved shape and the receiving portion 213b that continues to the protruding portion 213a and has a concave shape matching the exterior shape of the protruding portion 212a. The connecting portions 212 and 213 are arranged to overlap with each other along the axial direction X and the circumferential direction C while also being connected to each other by the biodegradable polymer 221. As a result, it is possible to appropriately maintain the connected state of the connecting portions 212 and 213 until the biodegradable polymer 221 is degraded.

Furthermore, the link portions 220 are provided with the coating layer 222. Since a medicine capable of preventing proliferation of a neointima is slowly eluted from the coating layer 222, it is possible to further inhibit or prevent restenosis of a lesion area.

(Modification)

A stent according to a modification is a so-called fully biodegradable stent in which all of the parts or members forming the stent including the strut and the link portions are formed of biodegradable polymer. Since the stent is fully degraded in a living body after the stent is indwelled in a lesion area, and after a predetermined time elapses, the indwelled object does not remain in a living body and is minimally invasive.

Materials described in the aforementioned embodiment may be employed as the biodegradable polymer. The strut is preferably formed of a biodegradable material degraded later than the biodegradable polymer of the link portion. As a result, it is possible to allow the stent to smoothly follow a shape of a lumen of a living body by increasing flexibility of the stent after connection of the link portion is released. As a result, it is possible to maintain an open state of the lesion area while supporting a lumen of a living body in a minimal invasive manner for a long time.

Similar to the aforementioned embodiment, the strut may have the annular portions and the helical portion. Alternatively, the strut may have only the helical portion without the annular portions.

Similar to the aforementioned embodiment, at least one of a plurality of link portions may be provided with the first and second connecting portions and the biodegradable material. Similar to the link portion 230 of the aforementioned embodiment, the link portion may be formed integrally with the strut.

The stent according to the modification is formed of biodegradable polymer. Since the stent formed of polymer has strength lower than that of the stent formed of a metal material, it is rather easily twisted. In this manner, even in the stent that is rather easily twisted, the stent is not so easily twisted with respect to the balloon. Therefore, it is possible to inhibit or prevent a twist of the stent at the time of expansion of the stent and prevent a collapse of the shape of the indwelled stent.

While the stent delivery system according to the embodiment and modification has been described above, the present invention is not limited to each configuration described above, and may be appropriately changed within the scope of the claims.

For example, the helical extending direction of the helical portion of the stent according (the second circumferential direction as seen from the proximal end side in the axial direction) is not limited to the direction described in the embodiment and the modification as long as it is opposite to the balloon folding direction (the first circumferential direction as seen from the proximal end side of the axial direction). That is, the helical extending direction of the helical portion of the stent may be counterclockwise, and the balloon folding direction may be clockwise.

The helical portion of the stent may be formed in a helical shape that does not include the folded portion 210a described above in the embodiment and the modification.

The type of link portion is not limited to those described above in the embodiment and the modification. For example, in the aforementioned embodiment, similar to the link portion 220, the link portion 230 may include the first and second connecting portions 212 and 213 and the biodegradable polymer 221.

The arrangement of the link portion may also be changed without being limited to those of the embodiment and the modification.

The member connecting the first and second connecting portions 212 and 213 is not limited to the biodegradable polymer 221, and may be formed of a biodegradable metal material such as magnesium or zinc.

The exterior shapes of the protruding portion, the receiving portion, and the holding portion are not limited to those of the embodiment and the modification described above. For example, the protruding portion, the receiving portion, and the holding portion may have an arbitrary polygonal shape.

Furthermore, the stents described above include a type having no coating layer 222 and a type in which a medicine capable of preventing proliferation of a neointima is contained in the biodegradable polymer 221. In the latter case, the medicine is slowly eluted as the biodegradable polymer 221 is degraded. Therefore, it is possible to prevent restenosis of a lesion area.

The detailed description above describes embodiments and modifications of a stent delivery system and method representing examples of the inventive stent delivery system and method disclosed here. The invention is not limited, however, to the precise embodiments and modifications described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery system comprising:
a balloon catheter comprised of an elongated shaft and an inflatable/deflatable balloon provided at a distal end side of the shaft;
a stent provided on an outer surface of the balloon while the balloon is deflated;

the deflated balloon comprising a plurality of limb portions folded at a plurality of folding pleats that extend along an axial direction of the shaft;

the plurality of limb portions being folded in a first circumferential direction to surround the shaft as seen from a proximal end side of the shaft in the axial direction; and the stent being comprised of a strut that includes a helical portion formed in a helical shape and helically extending along a second circumferential direction opposite to the first circumferential direction as seen from the proximal end side of the shaft in the axial direction centered on an axis extending along the axial direction of the shaft.

2. The stent delivery system according to claim 1, wherein at least a part of the stent is formed of polymer.

3. The stent delivery system according to claim 2, wherein the stent is formed of biodegradable polymer.

4. The stent delivery system according to claim 2, wherein the helical portion is comprised of neighboring helical parts, the stent further comprising link portions that connect neighboring helical parts, the link portions being made at least in part of polymer.

5. The stent delivery system according to claim 2, wherein the helical portion is comprised of neighboring helical parts, the stent further comprising link portions that connect neighboring helical parts, at least one of the link portions being made of the polymer, and the helical parts being formed of a metal material.

6. The stent delivery system according to claim 5, further comprising a coat on a surface of the polymer, the coat containing a medicine that prevents proliferation of a neointima.

7. The stent delivery system according to claim 5, wherein:
at least one of the link portions includes a first connecting portion provided integrally with one of the helical parts and a second connecting portion provided integrally with another of the helical parts neighboring the one helical part, the first and second connecting portions facing each other, and the biodegradable polymer being interposed between the first connecting portion and the second connecting portion to connect the first connecting portion and the second connecting portion to each other;
the first connecting portion includes a protruding portion that protrudes toward the second connecting portion and has a rounded curved shape and a receiving portion that continues from the first protruding portion and has a concave shape matching an exterior shape of the second protruding portion;
the first connecting portion includes a protruding portion that protrudes toward the first connecting portion and has a rounded curved shape and a receiving portion that continues from the second protruding portion and has a concave shape matching an exterior shape of the first protruding portion; and
the first connecting portion and the second connecting portion are arranged to overlap with each other along the axial direction and a circumferential direction of the shaft while being connected by the biodegradable polymer.

8. The stent delivery system according to claim 7, wherein the link portions are provided with a coat containing a medicine that prevents proliferation of a neointima on a surface of the polymer.

9. A stent delivery system comprising:
an inner tube positioned inside an outer tube, with a lumen between the inner tube and the outer tube, the outer tube possessing a distal end portion, and the inner tube possessing a distal end portion;

a balloon possessing an outer surface, an interior, a proximal end portion fixed to the distal end portion of the outer tube, and a distal end portion fixed to the distal end portion of the inner tube, the lumen between the inner and outer tubes communicating with the interior of the balloon to introduce fluid into the balloon to outwardly expand the balloon from a deflated state to an inflated state;

the balloon in the deflated state comprising a plurality of circumferentially spaced apart limb portions each folded at a respective folding pleat in a first circumferential direction as viewed from the proximal end portion of the balloon along an axial direction of the balloon so that the limb portions are in an overlying position in which the limb portions are in overlying relation to an underling portion of the balloon, the limb portions moving in a second circumferential direction opposite the first circumferential direction and away from the overlying position when the fluid is introduced into the balloon and the balloon outwardly expands from the deflated state toward the inflated state;

a stent encircling the outer surface of the balloon in the deflated state, the stent possessing a proximal end portion and a distal end portion; and the stent being comprised of a strut that includes a helical portion, the helical portion extending helically in the second circumferential direction from a position adjacent the proximal end portion of the stent toward the distal end portion of the stent as viewed from the proximal end portion of the balloon along an axial direction of the balloon.

10. The stent delivery system according to claim 9, wherein the strut comprises a first annular portion at the proximal end portion of the stent and a second annular portion at the distal end portion of the stent, the helical portion extending from the first annular portion to the second annular portion.

11. The stent delivery system according to claim 10, wherein the helical portion is comprised of neighboring helical parts, the first annular portion being connected to an adjacent one of the helical parts by a link portion, and the second annular portion being connected to an adjacent one of the helical parts by a link portion.

12. The stent delivery system according to claim 9, wherein the helical portion is comprised of neighboring helical parts, the stent further comprising a plurality of link portions that each connect neighboring helical parts.

13. The stent delivery system according to claim 12, wherein the link portions are made at least in part of polymer material, and the helical portion is made of a metal material.

14. The stent delivery system according to claim 12, wherein each of the link portions includes: a first connecting portion that is an integral extension of one of the helical parts; a second connecting portion that is an integral extension of another of the helical parts neighboring the one helical part; and a biodegradable polymer that positioned between the first and second connecting portions and overlapping each of the first and second connecting portions to connect the first and second connecting portions to each other.

15. The stent delivery system according to claim 14, wherein each of the first and second connecting portions overlap each other along the axial direction and a circumferential direction.

16. The stent delivery system according to claim 14, wherein:
- each of the first connecting portions includes a protruding portion that protrudes toward the second connecting portion and has a rounded curved shape and a receiving portion that continues from the first protruding portion and has a concave shape matching an exterior shape of the second protruding portion; and
- each of the first connecting portions includes a protruding portion that protrudes toward the first connecting portion and has a rounded curved shape and a receiving portion that continues from the second protruding portion and has a concave shape matching an exterior shape of the first protruding portion.

17. The stent delivery system according to claim 9, wherein the helical portion is comprised of neighboring helical parts connected to one another by circumferentially spaced apart link portions each made at least in part by a polymer material provided with a coating containing a medicine that prevents proliferation of a neointima.

18. A method comprising:
- delivering a stent to a lesion area in a lumen of a living body, the stent encircling an outer surface of a balloon while the balloon is in a deflated state, the balloon possessing a proximal end portion, the balloon in the deflated state comprising a plurality of circumferentially spaced apart limb portions each folded at a respective folding pleat in a first circumferential direction as viewed from the proximal end portion of the balloon along an axial direction of the balloon so that the limb portions are in an overlying position in which the limb portions are in overlying relation to an underling portion of the balloon, the stent possessing a proximal end portion and a distal end portion, the stent comprising a strut that includes a helical portion extending helically toward the distal end portion of the stent as viewed from the proximal end portion of the balloon along the axial direction of the balloon, the second circumferential direction being opposite the first circumferential direction;
- outwardly expanding the balloon that is in the deflated state so that the balloon undergoes outward expansion in which the balloon outwardly expands toward an expanded state; and
- the outward expansion of the balloon applying an outwardly directed force to the stent causing the limb portions of the stent to move in the second circumferential direction away from the overlying position as the stent expands outwardly.

19. The method according to claim 18, wherein the helical portion is comprised of neighboring helical parts connected to one another by link portions made at least in part from biodegradable material.

20. The method according to claim 18, wherein the strut also includes a first annular portion at a proximal end portion of the stent and a second annular portion at a distal end portion of the stent, the helical portion extending from the first annular portion to the second annular portion.

* * * * *